United States Patent
Ohmachi et al.

(10) Patent No.: US 10,485,853 B2
(45) Date of Patent: Nov. 26, 2019

(54) CHEESE AND METHOD FOR PRODUCING THE SAME

(75) Inventors: Aiko Ohmachi, Saitama (JP); Hiroaki Matsuyama, Saitama (JP); Yoshikazu Morita, Saitama (JP); Yuko Ishida, Saitama (JP); Takayuki Nara, Saitama (JP); Ken Kato, Saitama (JP); Atsushi Serizawa, Sapporo (JP); Hiroshi Ueno, Saitama (JP); Hiroshi Urazono, Saitama (JP)

(73) Assignee: MEGMILK SNOW BRAND CO., LTD., Hokkaido (JP)

(*) Notice: Subject to any disclaimer, the term of this patent is extended or adjusted under 35 U.S.C. 154(b) by 249 days.

(21) Appl. No.: 14/418,224

(22) PCT Filed: Jul. 31, 2012

(86) PCT No.: PCT/JP2012/069400
§ 371 (c)(1),
(2), (4) Date: Apr. 28, 2015

(87) PCT Pub. No.: WO2014/020684
PCT Pub. Date: Feb. 6, 2014

(65) Prior Publication Data
US 2015/0343029 A1 Dec. 3, 2015

(51) Int. Cl.
*A61K 38/46* (2006.01)
*A61K 38/44* (2006.01)
*A23C 19/06* (2006.01)
*A23C 19/05* (2006.01)
*A23C 19/076* (2006.01)
*A23C 19/082* (2006.01)

(52) U.S. Cl.
CPC .......... *A61K 38/465* (2013.01); *A23C 19/053* (2013.01); *A23C 19/063* (2013.01); *A23C 19/076* (2013.01); *A23C 19/082* (2013.01); *A61K 38/44* (2013.01); *A23V 2002/00* (2013.01); *A23V 2200/00* (2013.01); *A23V 2200/306* (2013.01); *A23V 2250/55* (2013.01); *C12Y 111/01007* (2013.01); *C12Y 301/27* (2013.01)

(58) Field of Classification Search
CPC .... A23C 19/063; A23C 19/053; A23C 19/082
See application file for complete search history.

(56) References Cited

U.S. PATENT DOCUMENTS

| 5,932,259 A | 8/1999 | Kato et al. |
| 5,976,597 A | 11/1999 | Takada et al. |
| 2006/0228345 A1 | 10/2006 | Motouri et al. |
| 2010/0209412 A1 | 8/2010 | Motouri et al. |
| 2010/0298228 A1* | 11/2010 | Serizawa ............... A21D 2/263 514/16.7 |
| 2011/0008361 A1* | 1/2011 | Bragger ............... A61K 35/20 424/157.1 |
| 2011/0151016 A1 | 6/2011 | McDonagh et al. |
| 2015/0182557 A1 | 7/2015 | Ohmachi et al. |
| 2015/0224178 A1 | 8/2015 | Ohmachi et al. |
| 2015/0297690 A1 | 10/2015 | Ohmachi et al. |
| 2015/0343030 A1 | 12/2015 | Ohmachi et al. |

FOREIGN PATENT DOCUMENTS

| EP | 0 704 218 | 4/1996 |
| JP | 8-151331 | 6/1996 |
| JP | 8-165249 | 6/1996 |
| JP | 9-191856 | 7/1997 |
| JP | 9-191858 | 7/1997 |
| JP | 10-007585 | 1/1998 |
| JP | 2004-238320 | 8/2004 |
| JP | 2005-60321 | 3/2005 |
| JP | 2011-519961 | 7/2011 |
| WO | 2010/028432 | 3/2010 |
| WO | 2010/058679 | 5/2010 |
| WO | 2011/060488 | 5/2011 |
| WO | 2011/060489 | 5/2011 |

OTHER PUBLICATIONS

Amornkul et al. "Utilization of Microfiltration or Lactoperoxidase System or Both for Manufacture of Cheddar Cheese from Raw Milk" J. Dairy Sci. 90:4988-5000.*

Morita et al., "Identification of Angiogenin as the Osteoclastic Bone Resorption-Inhibitory Factor in Bovine Milk," Bone, vol. 42, No. 2, pp. 380-387, 2008.

Extended European Search Report issued in EP Patent Application No. 12882348.1, dated Dec. 10, 2015.

Partial translation of Serizawa, "Development of 'Milk Basic Protein, MBP®'—A Novel Functional Food Ingredient for Bone Health," *The Third Symposium on Pharmaceutical Food Science Abstracts*, pp. 33-36, 2009.

Japanese Office Action issued in JP Patent Application No. 2014-527857, dated Jun. 8, 2016, along with an English-language translation.

Partial English-language translation of JP 2005-060321 (Mar. 10, 2005).

Serizawa, "Hone Kyoka Shokuhin Sozai 'Nyu Enkisei Tanpakushitsu' no Kaihatsu", *Abstracts of the 3rd Symposium on Pharmaceutical Food Science Yoshishu*, vol. 3 , pp. 33-36, 2009, including an English-language abstract.

(Continued)

*Primary Examiner* — Louise W Humphrey
*Assistant Examiner* — Stephen A Perkins
(74) *Attorney, Agent, or Firm* — Greenblum & Bernstein, P.L.C.

(57) ABSTRACT

The invention relates to a cheese includes angiogenin and/or angiogenin hydrolysate in an amount of 6.5 mg/100 g to 160 mg/100 g, and lactoperoxidase and/or lactoperoxidase hydrolysate in the mass ratio to the angiogenin and/or angiogenin hydrolysate of 0.3 to 33.

8 Claims, No Drawings

(56) References Cited

OTHER PUBLICATIONS

Morita et al., "Purification and identification of lactoperoxidase in milk basic proteins as an inhibitor of osteoclastogenesis", *Journal of Dairy Science*, vol. 94, No. 5, pp. 2270-2279, 2011.
International Search Report for PCT/JP2012/069400, dated Sep. 4, 2012.
International Preliminary Report on Patentability for PCT/JP2012/069400, dated Feb. 12, 2015.
Taiwanese Office Action issued with respect to Application No. 102126974 dated Jun. 6, 2017.

* cited by examiner

CHEESE AND METHOD FOR PRODUCING THE SAME

TECHNICAL FIELD

This invention relates to a novel cheese and a method for producing the same. The cheese includes a specific milk component, and may be useful for prevention and treatment of various bone diseases such as osteoporosis, fracture, rheumatism, and arthritis.

BACKGROUND ART

In recent years, various bone diseases, such as osteoporosis, fracture, and backache have increased on a global basis along with aging of society and the like, and have become a serious social problem. These diseases are caused by insufficient calcium intake, depression of calcium absorption ability, hormone imbalance after menopause, and the like. It is considered that increasing the body bone mass as much as possible and increase the maximum bone mass and the bone strength (bone density+bone quality) by promoting osteoblastic bone formation from the early stage of life is effective in preventing various bone diseases, such as osteoporosis, fracture, and backache. Note that the term "bone quality" refers to the bone microstructure, metabolic turnover, microfracture, and calcification. It is thought that various bone diseases, such as osteoporosis, fracture, and backache may be prevented by suppressing osteoclastic bone resorption. Bones are always repeatedly resorbed and formed in a balanced manner (remodeling). However, various bone diseases, such as osteoporosis, fracture, and backache may occur when bone resorption exceeds bone formation due to a change in hormone balance after menopause, and the like. Therefore, bones can be strengthened by suppressing osteoclastic bone resorption and maintaining the bone strength at a constant level.

In view of the above situation, a drug, food, drink, feed, or the like in which a calcium salt, such as calcium carbonate, calcium phosphate, or calcium lactate or a natural calcium product, such as whey calcium, bovine bone powder, or eggshell is added individually, has been ingested in order to strengthen bones. A drug, food, drink, feed, or the like that contains such a calcium product together with a substance having a calcium absorption-promoting effect, such as casein phosphopeptide or oligosaccharide has also been used to strengthen bones. However, the calcium absorption rate is 50% or less when a food or drink that contains a calcium salt or a natural calcium product is ingested, and the large part of the calcium ingested may be discharged from the body without being absorbed. Moreover, even if calcium is absorbed into the body, it does not necessarily exhibit the bone metabolism-improving effect or a bone-strengthening effect, since the affinity to bones may differ according to its form or the type of nutritional ingredient ingested together. An estrogen product, an active vitamin $D_3$ product, a vitamin $K_2$ product, a bisphosphonate product, a calcitonin product, and the like have been known as a drug for treating osteoporosis or strengthening bones, and new drugs such as an anti-RANKL antibody have been developed. However, these drugs may bring side effects such as buzzing in the ear, a headache, or loss of appetite. Moreover, the above substances are in a situation that they cannot be added to a food or drink at present from the viewpoint of safety, cost, and the like. Therefore, in light of the nature of various bone diseases, such as osteoporosis, fracture, and backache, development of such a food or drink that can be administered orally for a long time, increases the bone strength by promoting bone formation and suppressing bone resorption, and may be expected to have the effect of preventing or treating the various bone diseases has been desired.

PRIOR-ART DOCUMENT

Patent Document

[Patent Document 1] JP-A-H08-151331
[Patent Document 2] JP-A-H10-7585
[Patent Document 3] JP-A-2004-238320
[Patent Document 4] JP-A-2005-60321

SUMMARY OF THE INVENTION

Problems to be Solved by the Invention

The invention relates to providing a cheese that may be useful for prevention and treatment of various bone diseases such as osteoporosis, fracture, rheumatism, and arthritis.

Means for Solving the Problems

The present inventors have found that the bone density can be effectively increased by ingesting a cheese that includes angiogenin and/or angiogenin hydrolysate, and includes lactoperoxidase and/or lactoperoxidase hydrolysate in a specific mass ratio with respect to angiogenin and/or angiogenin hydrolysate. This finding has led to the completion of the invention.

Specifically, the invention includes following aspects:

(1) A cheese including angiogenin and/or angiogenin hydrolysate in an amount of 6.5 mg/100 g to 160 mg/100 g and lactoperoxidase and/or lactoperoxidase hydrolysate in the mass ratio to the angiogenin and/or angiogenin hydrolysate of 0.3 to 33.

(2) A method of preventing bone diseases including ingesting the cheese according to (1) in an amount of 20 g/day or more.

(3) A method of producing the cheese according to (1), including mixing angiogenin and/or angiogenin hydrolysate and lactoperoxidase and/or lactoperoxidase hydrolysate with a raw material cheese and/or a cheese curd.

(4) A method of producing the cheese according to (1), including mixing a raw material cheese with angiogenin and/or angiogenin hydrolysate and lactoperoxidase and/or lactoperoxidase hydrolysate, and emulsifying and cooling the mixture.

Effects of the Invention

The cheese of the invention exhibits a bone-strengthening effect, and may be useful for prevention and treatment of various bone diseases such as osteoporosis, fracture, rheumatism, and arthritis.

EMBODIMENTS FOR CARRYING OUT THE INVENTION

A cheese of the invention is characterized in that the cheese includes angiogenin and/or angiogenin hydrolysate in a specific amount, and further includes lactoperoxidase and/or lactoperoxidase hydrolysate in a specific mass ratio with respect to angiogenin and/or angiogenin hydrolysate.

A cheese generally contains angiogenin and/or angiogenin hydrolysate in an amount of about 1.1 to 6.3 mg/100 g, and lactoperoxidase and/or lactoperoxidase hydrolysate in an amount of about 2.7 to 189 mg/100 g.

In contrast, the cheese of the invention is added with angiogenin and/or angiogenin hydrolysate and lactoperoxidase and/or lactoperoxidase hydrolysate, and the cheese contains angiogenin and/or angiogenin hydrolysate in an amount of 6.5 mg/100 g to 160 mg/100 g, and lactoperoxidase and/or lactoperoxidase hydrolysate in a mass ratio with respect to angiogenin and/or angiogenin hydrolysate of 0.3 to 33.

A fraction containing angiogenin and/or angiogenin hydrolysate that is prepared from milk of a mammal, such as human, cow, buffalo, goat, or sheep, a fraction containing lactoperoxidase and/or lactoperoxidase hydrolysate that is prepared from milk of a mammal, such as human, cow, buffalo, goat, or sheep, a fraction containing angiogenin and/or angiogenin hydrolysate that is produced by genetic engineering, a fraction containing lactoperoxidase and/or lactoperoxidase hydrolysate that is produced by a genetic engineering, angiogenin and/or angiogenin hydrolysate purified from blood or an organ, lactoperoxidase and/or lactoperoxidase hydrolysate purified from blood or an organ, or the like may be used as the angiogenin and/or angiogenin hydrolysate and the lactoperoxidase and/or lactoperoxidase hydrolysate included in the cheese of the invention. A commercially available purified angiogenin or lactoperoxidase reagent may also be used.

The cheese of the invention may include angiogenin hydrolysate or lactoperoxidase hydrolysate obtained by digesting of a fraction containing angiogenin, an angiogenin reagent, a fraction containing lactoperoxidase, a lactoperoxidase reagent, or the like using one or more proteases.

The cheese of the invention may include a protein material prepared by extracting a fraction containing angiogenin and/or angiogenin hydrolysate and lactoperoxidase and/or lactoperoxidase hydrolysate directly from milk or a material derived from milk, such as skim milk or whey. Such a protein material may be prepared as follows, for example. Specifically, milk or a material derived from milk is brought into contact with a cation-exchange resin, and milk-derived proteins adsorbed on the resin is eluted at a salt concentration of 0.1 to 2.0 M, desalted and concentrated using a reverse osmosis membrane, an electrodialysis membrane, an ultrafiltration membrane, a microfiltration membrane, or the like, and optionally subjected to proteolysis to a molecular weight of 8000 or less using a protease, such as trypsin, pancreatin, chymotrypsin, pepsin, papain, kallikrein, cathepsin, thermolysin, or V8 protease. When subjecting to proteolysis using a protease, the lower limit of the molecular weight is preferably 500 or more. The protein material thus obtained may be dried by freeze-drying, spray drying, or the like, and the dried product may be incorporated in the cheese.

The cheese of the invention is produced by adding angiogenin and/or angiogenin hydrolysate, and lactoperoxidase and/or lactoperoxidase hydrolysate and a protein material that contains angiogenin and/or angiogenin hydrolysate and lactoperoxidase and/or lactoperoxidase hydrolysate, or the like to a raw material cheese so that the cheese includes angiogenin and/or angiogenin hydrolysate in an amount of 6.5 mg to 160 mg/100 ml, and includes lactoperoxidase and/or lactoperoxidase hydrolysate in a mass ratio with respect to angiogenin and/or angiogenin hydrolysate of 0.3 to 33.

As shown in the test examples described below, when the cheese includes angiogenin and/or angiogenin hydrolysate and lactoperoxidase and/or lactoperoxidase hydrolysate as described above, the bone-strengthening effect can be obtained more effectively than the case of ingesting angiogenin and/or angiogenin hydrolysate or lactoperoxidase and/or lactoperoxidase hydrolysate separately.

The cheese of the invention may be produced in the usual manner as long as the cheese includes the angiogenin and/or angiogenin hydrolysate and lactoperoxidase and/or lactoperoxidase hydrolysate in specific amounts, respectively. The term "cheese" used herein includes all types of cheese such as natural cheese, so-called processed cheese preparation which is a food using processed cheese, spreadable processed cheese, processed cheese food specified by the Codex Standard, milk, or the like as a main raw material. For example, natural cheese, such as fresh (unripened) cheese such as cream cheese, mozzarella, ricotta, mascarpone and fromage blanc, white mold cheese such as Camembert and Brie, blue mold cheese such as Gorgonzola, Stilton and Roquefort, washed rind cheese such as Livarot, semi-hard cheese such as Provolone and Gouda, and hard cheese such as Grana, Emmentaler and Cheddar, processed cheese produced using natural cheese, cheese-like food produced using oils and fats polysaccharides and the like, can be given.

In the case of Gouda cheese, for example, milk that is adjusted in fat content to 2.8% is used as a raw material, and angiogenin and/or angiogenin hydrolysate is added thereto in the specific amount, and lactoperoxidase and/or lactoperoxidase hydrolysate is further added in the mass ratio to angiogenin and/or angiogenin hydrolysate of the specific range. The mixture is sterilized at 77° C. for 15 seconds, and cooled. A starter, rennet, and the like are added thereto, and stirred. The mixture is then allowed to stand for about 30 minutes, and the whey is removed to prepare cheese curds. After the cheese curds are optionally added with salt, Gouda cheese can be produced through molding the cheese curds.

In the case of cottage cheese, cream or the like is used as a raw material, angiogenin and/or angiogenin hydrolysate is added thereto in the specific amount, and lactoperoxidase and/or lactoperoxidase hydrolysate is further added in the mass ratio to angiogenin and/or angiogenin hydrolysate of the specific range. The mixture is uniformly added to cheese curds to be able to produce cottage cheese. Examples of the raw material used for producing the cheese of the invention include milk of a mammal, such as cow, buffalo, goat, or sheep, milk thereof in which the fat content is adjusted, cream prepared from such mammal milk, and the like.

The cheese of the invention may be produced as described below. When producing processed cheese as the cheese of the invention, for example, as an emulsifying salt, sodium citrate, sodium monophosphate, sodium polyphosphate, or the like is added to a raw material cheese in an amount of about 2%. After the addition of water in an amount of about 10%, angiogenin and/or angiogenin hydrolysate is added to the mixture in the specific amount, and lactoperoxidase and/or lactoperoxidase hydrolysate is further added to the mixture in the mass ratio to angiogenin and/or angiogenin hydrolysate of the specific range. The mixture is emulsified at 85° C. in the usual manner, and the emulsion is placed into a carton, and cooled to 5° C. to be able to produce the processed cheese.

As a method of mixing angiogenin and/or angiogenin hydrolysate in the specific amount and lactoperoxidase and/or lactoperoxidase hydrolysate in the specific mass ratio to the processed cheese, it may be possible to use a cheese mixture which is previously prepared by added angiogenin and/or angiogenin hydrolysate and lactoperoxidase and/or lactoperoxidase hydrolysate as a raw material cheese, or to mix appropriate quantities of angiogenin and/or angiogenin hydrolysate and lactoperoxidase and/or lactoperoxidase hydrolysate with a raw material of the processed cheese.

It may be possible that the cheese of the invention may be added with a raw material or the like that is commonly used for a food or drink, such as a saccharide, a lipid, a protein, a vitamin, a mineral, or a flavor, in addition to angiogenin and/or angiogenin hydrolysate, lactoperoxidase and/or lactoperoxidase hydrolysate, other than the above raw material, cheese curd and raw material cheese, and may also be added with another bone-strengthening component such as calcium, vitamin D, vitamin K, or isoflavone.

The cheese of the invention can strengthen bones when administered orally in an amount of 20 g or more per kg of body weight, as shown in the animal experiments described below. Since the intake for the experiment animal corresponds to the intake for adults in terms of blood drug concentration (see Mitsuyoshi Nakajima (1993), "*Yakkou Hyoka* Vol. 8", Hirokawa-Shoten Ltd., pp. 2-18), it is expected that bones can be strengthened, and especially various bone diseases, such as osteoporosis, fracture, rheumatism, and arthritis can be prevented or treated by ingesting the cheese of the invention in an amount of 20 g/day or more per adult.

The invention is further described below in more detail by way of reference examples, examples, and test examples. Note that the following examples are intended for illustration purposes only, and should not be construed as limiting the invention.

Reference Example 1

Preparation (1) of Angiogenin Fraction

A column filled with 30 kg of cation-exchange resin (Sulfonated Chitopearl; manufactured by Fuji Spinning Co., Ltd.) was thoroughly washed with deionized water, and 1000 liters of unpasteurized skim milk (pH 6.7) was then applied to the column. After thoroughly washing the column with deionized water, the absorbed protein was eluted with a linear gradient of 0.1 to 2.0 M sodium chloride. The elution fraction containing angiogenin was fractionated using an S-Sepharose cation-exchange chromatography (manufactured by Amersham Bioscientific), and the resulted angiogenin-containing fraction was heat-treated at 90° C. for 10 minutes, and centrifuged to remove a precipitate. The angiogenin-containing fraction was further subjected to gel filtration chromatography (column: Superose 12). The eluate obtained was desalted using a reverse osmosis membrane, and the desalted eluate was freeze-dried to obtain 16.5 g of an angiogenin fraction having an angiogenin purity of 90%. These successive operations were repeated 30 times.

Reference Example 2

Preparation (2) of Angiogenin Fraction

A column filled with 10 kg of Heparin Sepharose (manufactured by GE Healthcare) was thoroughly washed with deionized water, and 500 liters of unpasteurized skim milk (pH 6.7) was then applied to the column. After thoroughly washing the column with a 0.5 M sodium chloride solution, the absorbed protein was eluted with a 1.5 M sodium chloride solution. The eluate was desalted using a reverse osmosis membrane, and the desalted eluate was freeze-dried to obtain 18 g of an angiogenin fraction having an angiogenin purity of 5%. The above successive operations were repeated 50 times.

Reference Example 3

Preparation of Lactoperoxidase Fraction

A column (diameter: 5 cm, height: 30 cm) filled with 600 g of cation-exchange resin (Sulfonated Chitopearl; manufactured by Fuji Spinning Co., Ltd.) was thoroughly washed with deionized water, and 360 liters of unpasteurized skim milk (pH 6.7) was applied to the column at a flow rate of 25 ml/min. After thoroughly washing the column with deionized water, the absorbed protein was eluted with a 0.02 M carbonate buffer (pH 7.0) containing 2.0 M sodium chloride. The elution fraction containing lactoperoxidase was adsorbed on an S-Sepharose FF column (manufactured by Amersham Bioscientific), and the column was thoroughly washed with deionized water. After equilibration with a 10 mM phosphate buffer (pH 7.0), the adsorbed fraction was eluted with a linear gradient of 0 to 2.0 M sodium chloride to collect a fraction containing lactoperoxidase. The fraction was subjected to gel filtration chromatography using a HiLoad 16/60 Superdex 75 pg (manufactured by Amersham Bioscientific). The eluate obtained was desalted using a reverse osmosis membrane, and freeze-dried to obtain 27 g of a lactoperoxidase fraction having a lactoperoxidase purity of 90%. These successive operations were repeated 25 times.

Measurement of Angiogenin and Lactoperoxidase Contained in Cheese

The content of angiogenin, angiogenin hydrolysate, lactoperoxidase and lactoperoxidase hydrolysate in the cheese was measured according to the method described in JP-A-2008-164511 with modification. Specifically, 190 mg of the cheese was added to 65 ml of ultrapure water, and a $1/1000$-equivalent amount of formic acid was added to the mixture to prepare a sample solution. Ten microliters (10 µl) of the sample solution was dried up, and dissolved in 20 µl of 0.1 M ammonium bicarbonate containing 8 M urea and 1 mM tris(carboxyethyl)phosphine (TCEP). The solution was heated at 56° C. for 30 minutes. After returning the solution to room temperature, 5 µl of a 100 mM iodoacetamide solution was added to the solution, and the mixture was reacted for 30 minutes in the dark. After the addition of 54 µl of ultrapure water, 10 µl of 0.1 µg/ml trypsin and 10 µl of 0.1 µg/ml Lysyl Endopeptidase were added to the mixture. The mixture was reacted at 37° C. for 16 hours. The reaction was then terminated by adding 3 µl of formic acid and used as a sample peptide solution for measurement. The sample solution was diluted 6-fold with 10 fmol/µl internal standard peptide solution containing 0.1% formic acid, 0.02% trifluoroacetic acid (TFA), and 2% acetonitrile, and 2.5 µl of the diluted solution was subjected to LC/MS/MS analysis.

The peptides were separated by gradient elution using an HPLC system. More specifically, the peptides were separated using a column (MAGIC C18, 0.2 mm (ID)×50 mm) equipped with a 5 µl-peptide trap on a MAGIC 2002 HPLC system at a flow rate of 2 µl/min. A solution A (2% acetonitrile-0.05% formic acid) and a solution B (90% acetonitrile-0.05% formic acid) were used as eluants for HPLC. Gradient elution was conducted under the elution condition of increasing the relative volume of solution B from 2% to 65% over 20 minutes.

As object ions for measuring lactoperoxidase, parent ion was $NH_2$-IHGFDLAAINLQR-COOH (m/z 734.4), and the MS/MS target ion was $NH_2$-IHGFDLA-COOH (m/z 754.4).

As object ions for measuring angiogenin, parent ion was NH$_2$-YIHFLTQHYDAK-COOH (m/z 768.8), and the MS/MS target ion was NH$_2$-FLTQHYDAK-COOH (m/z 1122.8). Regarding the internal standard peptide parent ion was NH$_2$-ETTVFENLPEK-COOH (wherein, P was labeled with $^{13}$C and $^{15}$N) (m/z 656.9.), and the MS/MS target ion was NH$_2$-FENLPEK-COOH (wherein, P was labeled with $^{13}$C and $^{15}$N) (m/z 882.4).

A system "LCQ Advantage" was used for MS. The peak area of each protein was calculated from the resulting chromatogram, and the concentration was calculated from the ratio with respect to the internal standard peptide.

Example 1

Eight point eight grams (8.8 g) of Gouda cheese and 8.8 g of cheddar cheese were mixed. Next, 0.4 g of sodium citrate as emulsifying salt is added thereto, and 2 g of water, 35 mg of the angiogenin fraction obtained in Reference Example 1 and 5 mg of the lactoperoxidase fraction obtained in Reference Example 3 were further added to the mixture. The mixture was emulsified at 85° C. in the usual manner. After the completion of the emulsification, the emulsion was placed into a carton, and cooled at 5° C. for two days and nights to obtain a cheese (example product 1). The resulting cheese contained angiogenin and/or angiogenin hydrolysate in an amount of 160 mg/100 g, and the mass ratio of lactoperoxidase and/or lactoperoxidase hydrolysate to angiogenin and/or angiogenin hydrolysate in the cheese was 0.3.

Example 2

Eight point eight grams (8.8 g) of Gouda cheese and 8.8 g of cheddar cheese were mixed. Next, 0.4 g of sodium citrate as emulsifying salt is added thereto, and 2 g of water, 20 mg of the angiogenin fraction obtained in Reference Example 2 and 40 mg of the lactoperoxidase fraction obtained in Reference Example 3 were mixed therewith. The mixture was emulsified at 85° C. in the usual manner. After the completion of the emulsification, the emulsion was placed into a carton, and cooled at 5° C. for two days and nights to obtain a cheese (example product 2). The resulting cheese contained angiogenin and/or angiogenin hydrolysate in an amount of 6.5 mg/100 g, and the mass ratio of lactoperoxidase and/or lactoperoxidase hydrolysate to angiogenin and/or angiogenin hydrolysate in the cheese was 33.

Example 3

Eight point eight grams (8.8 g) of Gouda cheese and 8.8 g of cheddar cheese were mixed. Next, 0.4 g of sodium citrate as emulsifying salt is added thereto, and 2 g of water, 20 mg of the angiogenin fraction obtained in Reference Example 1 and 40 mg of the lactoperoxidase fraction obtained in Reference Example 3 were mixed therewith. The mixture was emulsified at 85° C. in the usual manner. After the completion of the emulsification, the emulsion was placed into a carton, and cooled at 5° C. for two days and nights to obtain a cheese (example product 3). The resulting cheese contained angiogenin and/or angiogenin hydrolysate in an amount of 90 mg/100 g, and the mass ratio of lactoperoxidase and/or lactoperoxidase hydrolysate to angiogenin and/or angiogenin hydrolysate in the cheese was 2.3.

Comparative Example 1

Eight point eight grams (8.8 g) of Gouda cheese and 8.8 g of cheddar cheese were mixed. Next, 0.4 g of sodium citrate as emulsifying salt is added thereto, and 2 g of water, 15 mg of the angiogenin fraction obtained in Reference Example 2 and 45 mg of the lactoperoxidase fraction obtained in Reference Example 3 were mixed therewith. The mixture was emulsified at 85° C. in the usual manner. After the completion of the emulsification, the emulsion was placed into a carton, and cooled at 5° C. for two days and nights to obtain a cheese (comparative example product 1). The resulting cheese contained angiogenin and/or angiogenin hydrolysate in an amount of 5.0 mg/100 g, and the mass ratio of lactoperoxidase and/or lactoperoxidase hydrolysate to angiogenin and/or angiogenin hydrolysate in the cheese was 46.

Comparative Example 2

Eight point eight grams (8.8 g) of Gouda cheese and 8.8 g of cheddar cheese were mixed. Next, 0.4 g of sodium citrate as emulsifying salt is added thereto, and 2 g of water, 38 mg of the angiogenin fraction obtained in Reference Example 1 and 2 mg of the lactoperoxidase fraction obtained in Reference Example 3 were mixed therewith. The mixture was emulsified at 85° C. in the usual manner. After the completion of the emulsification, the emulsion was placed into a carton, and cooled at 5° C. for two days and nights to obtain a cheese (comparative example product 2). The resulting cheese contained angiogenin and/or angiogenin hydrolysate in an amount of 165 mg/100 g, and the mass ratio of lactoperoxidase and/or lactoperoxidase hydrolysate to angiogenin and/or angiogenin hydrolysate in the cheese was 0.2.

Test Example 1

The bone-strengthening effects of the example products 1 to 3 and the comparative example products 1 and 2 were determined by animal experiments. C3H/HeJ mice (5 weeks old, male) were used for the animal experiments. Each cheese of the example products 1 to 3 and the comparative example products 1 and 2 was added to hot water (60° C.) so that the content of the cheese was 20%, and the mixture was homogenously stirred. After 1 week acclimation, the mice were divided into six groups (10 mice/group). The mice were orally administered each of the example products 1 to 3 and the comparative example products 1 and 2 in an amount of 20 g (as cheese)/day per 1 kg of mouse weight daily in two divided dose using a tube. The control group was not administrated any example products 1 to 3 and the comparative example products 1 and 2. After completion of administration (second week), the bone density of the right tibia of each mouse was measured using a micro-CT (manufactured by Rigaku Corporation). The results are shown in Table 1. As shown in Table 1, the groups that were orally administered the example products 1 to 3 showed a significant increase in bone density as compared with the control group and the comparative example groups that were orally administered the comparative example product 1 or 2.

TABLE 1

| | Bone density (mg/cm³) |
|---|---|
| Control group | 1237 ± 8 |
| Example product 1 | 1265 ± 10 |
| Example product 2 | 1271 ± 14 |
| Example product 3 | 1267 ± 9 |
| Comparative example product 1 | 1243 ± 5 |
| Comparative example product 2 | 1242 ± 7 |

Reference Example 4

A column (diameter: 4 cm, height: 30 cm) filled with 400 g of cation-exchange resin (Sulfonated Chitopearl; manufactured by Fuji Spinning Co., Ltd.) was thoroughly washed with deionized water, and 40 liters of unpasteurized skim milk (pH 6.7) was applied to the column at a flow rate of 25 ml/min. After thoroughly washing the column with deionized water, proteins adsorbed on the resin were eluted using a 0.02 M carbonate buffer (pH 7.0) containing 0.78 M sodium chloride. The eluate was desalted using a reverse osmosis membrane, and the desalted eluate was freeze-dried to obtain 18 g of a powdery protein material (reference example product 4).

Reference Example 5

Four grams (4 g) of protein material of the reference example product 4 was dissolved in 800 ml of water. After the addition of trypsin (manufactured by Sigma), which is a protease, so as to obtain the final concentration of 0.03 wt %, the mixture was subjected to enzymatic treatment at 37° C. for 8 hours. After inactivating the protease through heat-treatment at 90° C. for 5 minutes, the mixture was freeze-dried to obtain 3.0 g of a powdery protein material (reference example product 5).

Example 4

Forty milligrams (40 mg) of the reference example product 4 was mixed with 3 g of 30% cream. The mixture was homogenously added to 17 g of cottage cheese curds to obtain a cheese (example product 4). The resulting cheese contained angiogenin and/or angiogenin hydrolysate in an amount of 13 mg/100 ml, and the mass ratio of lactoperoxidase and/or lactoperoxidase hydrolysate to angiogenin and/or angiogenin hydrolysate in the cheese was 5.2.

Example 5

Forty milligrams (40 mg) of the reference example product 5 was mixed with 3 g of 30% cream. The mixture was homogenously added to 17 g of cottage cheese curds to obtain a cheese (example product 5). The resulting cheese contained angiogenin and/or angiogenin hydrolysate in an amount of 12 mg/100 g, and the mass ratio of lactoperoxidase and/or lactoperoxidase hydrolysate to angiogenin and/or angiogenin hydrolysate in the cheese was 5.0.

Example 6

Forty milligrams (40 mg) of the reference example product 4 was added to 100 ml of milk that was adjusted in fat content to 2.8%, and the mixture was sterilized at 77° C. for 15 seconds. After cooling, starter, rennet, and the like were added thereto, and the mixture was allowed to stand for 30 minutes. After that, the whey was removed to prepare cheese curds. The cheese curds were salted, and the salted cheese curds were placed in a mold to obtain a cheese (example product 6). The resulting cheese contained angiogenin and/or angiogenin hydrolysate in an amount of 16 mg/100 g, and the mass ratio of lactoperoxidase and/or lactoperoxidase hydrolysate to angiogenin and/or angiogenin hydrolysate in the cheese was 5.3.

Comparative Example 3

Eight milligrams (8 mg) of the reference example product 4 and 32 mg of the lactoperoxidase fraction obtained in Reference Example 3 were mixed with 3 g of 30% cream. The mixture was homogenously added to 17 g of cottage cheese curds to obtain a cheese (comparative example product 3).

The obtained cheese contained angiogenin and/or angiogenin hydrolysate in an amount of 4.5 mg/100 g, and the mass ratio of lactoperoxidase and/or lactoperoxidase hydrolysate to angiogenin and/or angiogenin hydrolysate in the cheese was 39.

Test Example 2

The bone-strengthening effects of the example products 4 to 6 and the comparative example product 3 were determined by animal experiments. Forty eight SD female rats (51 weeks old) were used for the animal experiments.

Each of the example products 4 to 6 and the comparative example product 3 was added to hot water (60° C.) so that the content of the cheese was 20%, and the mixture was homogenously mixed and stirred.

The rats were divided into six groups (8 rats/group). Five groups underwent ovariectomy, and the remaining one group sham surgery. After a 4-week recovery period, the ovarectomized rats were orally administered the example products 4 to 6 or the comparative example product 3 in an amount of 20 g (as cheese) per 1 kg of rat weight daily in six divided dose using a tube. The control group was not administrated any example products 4 to 5 and the comparative example product 3. After a 4-week recovery period, the rats underwent sham surgery were fed for 16 weeks in the same manner as the control group. After completion of administration (sixteenth week), the bone density of the right tibia of each rat was measured using a micro-CT (manufactured by Rigaku Corporation).

The results are shown in Table 2. As shown in Table 2, the groups that were orally administered the example products 4 and 5 showed a significant increase in bone density as compared with the control group and the group that was orally administered the comparative example product 3. Moreover, the bone density approached that of the sham surgery group.

TABLE 2

| | Bone density (mg/cm³) |
|---|---|
| Control group | 550 ± 11 |
| Sham surgery group | 601 ± 10 |
| Example product 4 | 598 ± 9 |
| Example product 5 | 596 ± 8 |
| Example product 6 | 597 ± 12 |
| Comparative example product 3 | 553 ± 7 |

Example 7

Fifty milligrams (50 mg) of the reference example product 4 was added to 100 ml of milk that was adjusted in fat content to 3.6%, and the mixture was sterilized at 77° C. for 15 seconds. The mixture was then cooled. A starter, rennet, and the like were added thereto, and the mixture was allowed to stand for 40 minutes. A tarter, rennet, and the like, were added thereto and stirred, after that the mixture was allowed to stand for 40 minutes. The whey was then removed to prepare cheese curds. After the addition of 0.05% of blue mold (*P. roqueforti*) was added to the cheese curds at 0.05% with respect to the cards, the cheese curds were placed in a cheese hoop, and allowed to stand at 20° C. for 20 hours. The cheese curds were taken out from the hoop, and the surface of the cheese was rubbed with a salt for 3 days. After the completion of the salting, needling was conducted at the upper and lower sides of the cheese curds. After needling, the surface of the cheese was wrapped with a film, and the cheese was then matured at 8° C. for 60 days.

The obtained cheese contained angiogenin and/or angiogenin hydrolysate in an amount of 19 mg/100 g, and the mass ratio of lactoperoxidase and/or lactoperoxidase hydrolysate to angiogenin and/or angiogenin hydrolysate in the cheese was 5.1.

The invention claimed is:

1. A cheese comprising:
   i) angiogenin and/or angiogenin hydrolysate in an amount of 6.5 mg/100 g to 160 mg/100 g and
   ii) lactoperoxidase and/or lactoperoxidase hydrolysate in a mass ratio to the angiogenin and/or angiogenin hydrolysate of 0.3:1 to 33:1.

2. A method of treating bone diseases comprising ingesting the cheese according to claim 1 in an amount of 20 g/day or more.

3. A method of producing the cheese according to claim 1, comprising mixing angiogenin and/or angiogenin hydrolysate and lactoperoxidase and/or lactoperoxidase hydrolysate with a raw material cheese and/or a cheese curd.

4. A method of producing the cheese according to claim 1, comprising mixing a raw material cheese with angiogenin and/or angiogenin hydrolysate and lactoperoxidase and/or lactoperoxidase hydrolysate, emulsifying, and cooling the mixture.

5. The cheese according to claim 1, wherein the angiogenin and/or the lactoperoxidase is a hydrolysate.

6. The method according to claim 2, wherein the angiogenin and/or the lactoperoxidase is a hydrolysate.

7. The method according to claim 3, wherein the angiogenin and/or the lactoperoxidase is a hydrolysate.

8. The method according to claim 4, wherein the angiogenin and/or the lactoperoxidase is a hydrolysate.

* * * * *